United States Patent [19]

Rousso

[11] Patent Number: 4,628,921
[45] Date of Patent: Dec. 16, 1986

[54] UNILATERAL EXTERNAL FIXATION SYSTEM FOR SMALL BONES

[76] Inventor: Mauricio Rousso, 4/66 Lea Goldberg Street, Jerusalem 97 457, Israel

[21] Appl. No.: 656,926

[22] Filed: Oct. 2, 1984

[30] Foreign Application Priority Data

Oct. 3, 1983 [IL] Israel ........................................ 69888

[51] Int. Cl.⁴ ............................................... A61F 5/04
[52] U.S. Cl. .................................. 128/92 Z; 128/92 R
[58] Field of Search .................. 128/92 A, 92 R, 84 B

[56] References Cited

U.S. PATENT DOCUMENTS

| | | | |
|---|---|---|---|
| 1,201,864 | 10/1916 | Overmeyer | 128/92 A |
| 2,251,209 | 7/1941 | Stader | 128/92 A |
| 2,372,866 | 4/1945 | Tofflemire | 128/92 A |
| 2,406,987 | 9/1946 | Anderson | 128/92 A |
| 3,709,219 | 1/1973 | Halloran | 128/92 A |
| 4,187,841 | 2/1980 | Knutson | 128/92 A |
| 4,349,017 | 9/1982 | Sayegh | 128/92 A |
| 4,502,473 | 3/1985 | Harris et al. | 128/92 R |
| 4,554,915 | 11/1985 | Brumfield | 128/92 R |

FOREIGN PATENT DOCUMENTS

| | | | |
|---|---|---|---|
| 1569090 | 5/1969 | France | 128/92 A |
| 140329 | 2/1980 | German Democratic Rep. | 128/92 A |
| 2033758 | 5/1980 | United Kingdom | 128/92 A |

Primary Examiner—Robert Peshock
Assistant Examiner—Cary E. Stone
Attorney, Agent, or Firm—Browdy and Neimark

[57] ABSTRACT

A versatile unilateral fixation system for hand surgery includes a rod and at least first and second blocks with the distance between them being controllable by rotating the rod. Each block has at least one aperture through which a wire, which is adapted to be inserted into a hand bone segment, is securable by means of a setscrew. Additional blocks are includable to insert wires in different bone segments in different orientations.

17 Claims, 12 Drawing Figures

UNILATERAL EXTERNAL FIXATION SYSTEM FOR SMALL BONES

The present invention generally relates to fracture fixation devices and, more particularly, to a novel highly versatile external fixation system finding singular application in the treatment of injuries to small bones.

Injuries to the hand often produce severe and compound lesions. These include injuries to soft tissues, muscles, tendons and nerves hereafter also generally referred to as organs, as well as to joints and bones. Quite often the strategy and technique which is to be employed in treating one organ contradicts timewise or in other aspects the strategy and technique to be employed in treating other organ(s). For example, since lack of skin endangers the survival of deeper structures, resurfacing should be performed without delay. A progressing inflammation interferes with active and/or early passive exercises, which are essential to avoid edema, stiffness and/or chronic pain. At the same time osteoarticular loss must be aligned and fixed in correct position, while bone grafting is programmed. Healing of fractured bones requires extended rest, while tendon function dictates controlled early active movement.

While proper healing of any of the above-mentioned possible injuries presents a challenge to the medical profession, several different type injuries, as often occur simultanesoyly in the hand, produce an almost impossible task. At present choices are made which type injury should be treated first at the price of proper healing of less severe injuries. As a result dystrophy and fibrosis often occur in spite of the best effort set forth.

Herebefore external fixation devices, either of the unilateral or bilateral types, have been developed for fixation of large bones. However, to date a fixation device with a high degree of flexibility and ease of use is not in existence, nor has it been described in or suggested by the literature for application to small bones.

The present invention is directed to provide a versatile unilateral fixation system for hand surgery. The versatile unilateral fixation system comprises;

a rod element; and first and second blocks, each defining at least one aperture through which a wire is securable, the wire being adapted to have one end thereof secured within a hand bone, with the wires securable to the two blocks being secured in different bone segments, and means for releasably attaching the two blocks to said rod so that the wires attached to the blocks are at a preselected orientation, with the distance between said blocks on said rod being controllable by rotating said rod.

The rod is threaded about at least a part of its surface. It is a small diameter machine screw or bolt with fine threads. Each of the blocks is typically a small cube. Each has at least one hole to accommodate a wire, used in external fixation system, known as a Kirschner (K) wire. As is known, such wires have first ends which are threaded into bones adjacent the injury. At least one wire is releasably attached to each block while the two blocks are releasably securable to the rod. As will be pointed out hereafter, one (first) block, has a threaded hole through which the rod is threaded, while a second block has a blind hole through which the distal end of the rod extends, abutting the hole bottom. Each of the blocks has a threaded hole to accommodate a set screw to lock the block to the rod. With these two blocks and the simple rod, the K wires can be aligned in any desired orientation. Also the distance between the blocks and thus the K wires therein, can be easily adjusted to produce distraction or compression of the organs in which the K wires are secured. Additional blocks and rods with unique features are provided to form the novel fixation system particularly designed for treating injuries to the hand.

The novel features of the invention are set forth with particularity in the appended claims. The invention will best be understood from the following description when read in conjunction with the accompanying drawings.

Figure 1:
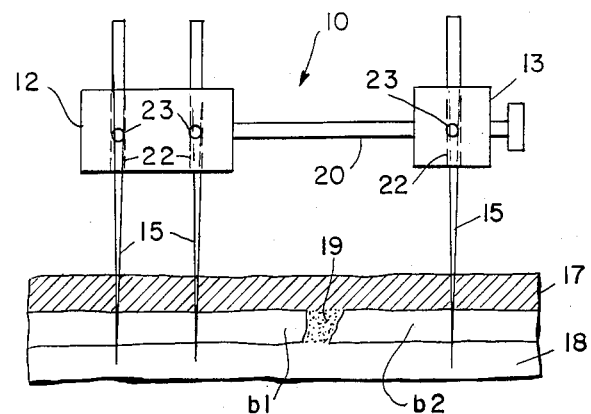
FIG. 1 is a general block diagram of a basic embodiment of the invention.
Figure 2:
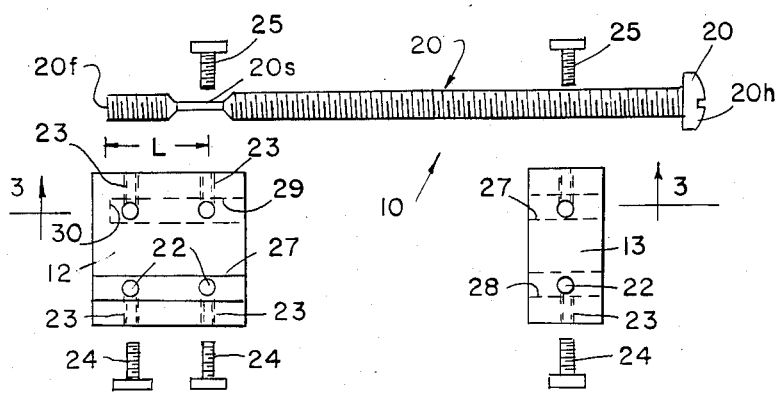
FIGS. 2 and 3 are top and cross-sectional views of a rod and two blocks, shown in FIG. 1.
Figure 3:
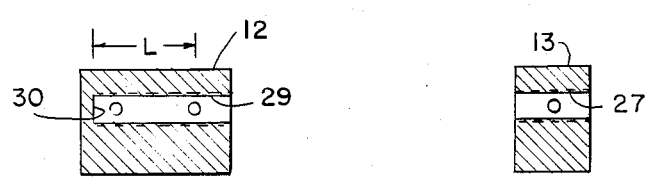

Attention is now directed to FIGS. 1, 2 and 3 in connection with which a basic embodiment of the invention will first be described. The unilateral external fixation system of the invention which is particularly designed for treating hand injuries and which will be hereafter simply referred to as the fixation system or simply the system, is designated in these Figures by 10. As shown in FIGS. 1 and 2 the system consists of two blocks 12 and 13 hereafter also referred to as cubes. Each is configured as will be explained hereafter in detail to be attached to at least one Kirschner or K-type wire 15. In FIG. 1 the two K wires 15 from block 12 are shown anchored at their proximal ends in bone b1 while the signal wire 15 from block 13 is anchored in bone b2. Layers 17 and 18 above and below these bones represent body organs while numeral 19 designates a normal joint or bone fracture between b1 and b2.

Forming an integral part of the fixation system 10 is a rod 20, which extends through block 13 and to block 12. As will be described the rod 20, which in practice may be a machine screw with fine threads, is used to releasably attach the blocks thereto. By a simple process the distance between the blocks can be adjusted to produce compression or distraction between bones b1 and b2. in order to attain the desired adjustment for proper injury treatment. To complete the description of FIG. 1 and before describing the blocks and the system in more details it should be pointed out that in FIG. 1 numerals 22 represent through holes extending from one side of each block assumed to be the top side to the opposite bottom side. It is through these holes that the K wires 15 which generally are in the order of not more than several millimeters 8 mm9 extend. For each hole 22 the block has a transverse threaded hole 23 used to accommodate a set screw 24 (see FIG. 2) to lock a K wire 15 to the block by pressing against it.

In FIG. 2, block 12 is shown with four holes 22 and block 13 with two holes 22. As will be clear from the following description, at any one application only half the number of holes 22 in each block can be used to accommodate K wires.

Each block in addition to holes 22 and set-screw holes 23 includes at least one and preferably more, transverse to both holes 22 and 23 in the plane of the latter. These holes are designed for the clamping or locking of a block to the rod 20. At any one time only one of these holes is used. In the novel system these holes, hereafter referred to as rod-support holes are of three types. One type of a rod-support hole designated in FIG. 2 by 22 is a through threaded hole. The other type designated by 28 is a through unthreaded or clearance hole for the rod, while the third type designated by 29 is a blind ended clearance hole, in that it is of diameter large enough to enable the rod to extend into it without threading, but does not extend through the entire block. That is, it is bottomed as indicated by 30 in FIG. 2 for block 12, and in FIG. 3 which is a cross-sectional view along lines 3—3 in FIG. 2. As seen in FIG. 2 block 12 includes holes 27 and 29 which are parallel to one another, while block 13 includes parallel rod-support holes 27 and 28.

As shown in FIGS. 2 and 3 the rod-support holes in each block, in addition to being parallel to one another extend in a plane in which set-screw openings 23 extend but in a direction transverse to the rod-support holes. Thus when rod 20 is threaded through a hole 27 a set-screw can be threaded through a hole 23 to lock the block to the rod. Likewise a rod extending through a hole 28 or 29 can be locked to the block by a set-screw. To distinguish between the set screws used to lock K wires in holes 15, which are designated by 24 from set screws for locking together the rod 20 to a block, the latter are designated by 25. However, this distinction is made for explanatory purposes only. Any set-screw hole 23 is designed to accommodate either a set-screw 24 or 25.

As shown in FIG. 2 the rod 20 is shaped with a reduced diameter at a distance L from its tip 20t. This distance L is equal to the distance from the bottom 30 of blind hole 29 to one of holes 23 (see FIG. 3). Consequently when the rod is inserted into a blind hole 29 with its tip 20t abutting against bottom 30 the rod's reduced diameter section 20s is aligned with one of the holes 23. This enables a set-screw 25 to press against the rod to lock it to the block. More importantly by slightly loosening the set-screw 25 within hole 23, but not enough so as to enable the rod to be extracted, the rod remains within the block, but is free to rotate therein. The important purpose of this feature will be described shortly.

The manner of using the novel fixation system will now be described. It is assumed that 3 K wires have been embedded, one in bone b2 (see FIG. 1) and two in bone b1 at a distance equal to the distance between two holes 22 in block 12. The rod 20 is first threaded through threaded hole 27 of block 13 toward head 20h. Then the K wire in bone b2 is inserted into hole 22 of block 13, which is not blocked by the rod in hole 27. That is it is inserted into hole 22 which is transverse to unused rod. Likewise, the two K wires in bone b1 are inserted through unobstructed wire holes 15 in block 12, which are transverse to unused rod-support hole 27. The rod is then inserted into hole 29 until its tip 20t presses against hole bottom 30. Set screws 25 are then used to releasably lock the two blocks to the rod 20. Clearly block unlocking from the rod is achieved by loosening the set screw 25.

It should be apparent that since the rod 20 is either threaded through a block, e.g. block 12 in a rod-support threaded hole 27 or is accommodated in a blind hole 29, such as in block 12, either block is rotatable about the block 360°. Thus the two-blocks can assume any angle with respect to one another. This is very significant since it enables the surgeon to insert K wires into bones in many different orientations. That is the K wires to be supported by the different blocks can lie in different planes. As to the embodiment described so far, the K wires to be supported by any one block are assumed to have their longitudinal axes in the same plane, since the longitudinal axes of holes 22 in any one block are in the same plane. However, as will be pointed out hereafter the invention is not limited thereto.

Let it be assumed that the fixation system 10, as shown in FIG. 2, is properly positioned with the blocks 12 and 13 locked onto rod 20 a proper distance, with K wires clamped thereto. Now, let it be assumed that due to healing requirements, compression or separation of bone segments is required. That is, bones b1 and b2 (FIG. 1) have to be brought closer or further apart. Such effects are easily attainable with the present system. Without disturbing the K wires the set screw 25 which locks rod 20 to block 13 is loosened to enable the rod to be further threaded in hole 27. Also set screw 25 which presses against rod section 20s to lock the rod to block 12 is loosened. However, it is only loosened sufficiently to enable the rod to rotate in hole 29, without being extractable therefrom. Thus the rod tip 20t remains bottomed to hole bottom 30. That is the relative position of block 12 on rod 20 remains the same. Thereafter the rod is turned, such as by inserting the tip of a screw driver into head 20h, while holding on to block 13. As the rod is turned, i.e. is threaded in hole 27 of block 12, in one or the other direction, thus producing the desired compression or distraction. Once achieved the two blocks are again locked to the rod by set screws 25.

It should be pointed out that for the arrangement shown in FIG. 2 in which the rod 20 is threaded through hole 27 of block 13 the two are threadably engaged and thus locked. Therefore if desired set screw 25 need not be used. However to secure the angular orientation of block 13 about the rod and thus with respect to block 12, it is preferred to use a set screw 25 to lock each block to the rod. Also if desired block 13 may be coupled to the rod through through-hole 28 rather than through threaded hole 27.

It should be pointed out that for distraction purposes if desired the two rod clamping set screws 25 may be totally loosened in block 13 even if the rod were to extend through a through-hole such as hole 28, and the same is true for the set screw 25 locking the rod 20 to block 12. The reason is that any distraction is partially overcome by the tendency of the organs to pull together. Thus, to ahcieve distraction the two blocks can be unlocked totally from the rod and then after spacing them the desired additional required distance to achieve the desired distraction. Only then are the blocks relocked by set screws 25.

As to compression, one should use a proximate block, i.e. one closer to the rod's head, such as block 13 which is lockable to the rod 20 by threads, i.e. through a threaded hole 27. As to the distal block 12 it should be locked to the rod through a blind hole, such as 29. In compression the set screw 25 in block 12 is only loosened sufficiently to allow the rod 20 to turn in hole 29 but not yet freed therefrom. This is achieved by releasing the set screw only slightly, while keeping its tip within the grooved section 20s of the rod. The compression is achieved by turning the rod to bring block 13, which is threaded thereto, closer to block 12.

Figure 4:
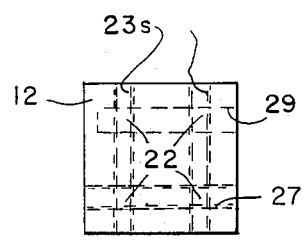
FIG. 4 is a top view of another embodiment of one of the blocks.

In FIG. 2 the set-screw holes 23 are shown extending only to the K wire holes 22. If desired holes 23 from opposite ends of the block may be formed by a single threaded hole. Thus, instead of the four holes 23 shown in FIG. 2 in block 12 two long threaded holes 23s may be formed as shown in FIG. 4. Therein the K wire holes 22 are shown simply as dots rather than through holes. As seen from FIG. 4 the two long holes 23s are on the same plane as the rod supporting holes 27 and 29 but transverse to the latter. If desired either of holes 23s may be used to thread the rod therethrough and use the holes 22 which extend through the other hole 23s to lock K-wires therein. Thus in a sense the block 12 can be thought of turned about by 90°.

It should be clear that block 13 which has two holes 22 can only support one K wire since the other hole 22 is blocked off by the rod. Likewise in block 12 with the four holes 22 only two holes 22 can be used to accommodate K wires since the other two are blocked off by the rod 20. Thus in any block only half the number of K-wires holes can be used to support K-wires.

In the blocks described so far, the longitudinal axes of holes 22 were shown as all being parallel to one another. Blocks with such holes can only be used if the longitudinal axes of all the K wires are parallel. However, the invention is not limited thereto. To support oblique K-wires one or more holes 22 in a block may extend obliquely to other holes 22. Also a block may possess more than four holes 22.

Figure 5A:
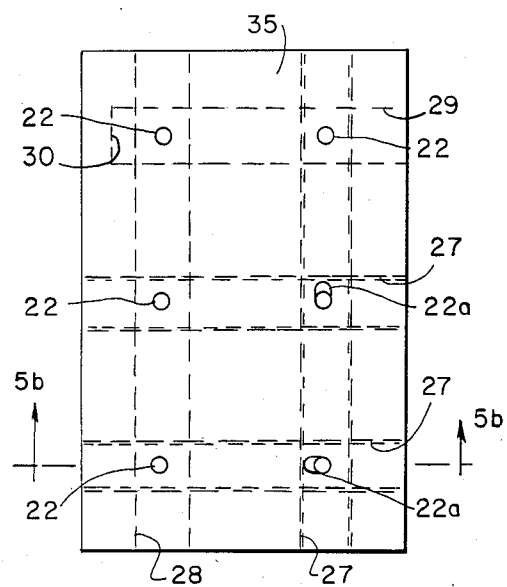
FIGS. 5a and 5b are views of yet another block.
Figure 5B:
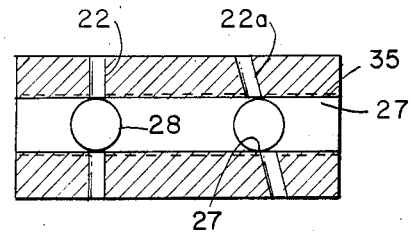

A block with six holes for K-wires is shown in top view in FIG. 5a and in partial cross-sectional view in FIG. 5b, which is a view along lines 5b—5b in FIG. 5a. The block is designated by 35. As shown it includes several rod-support holes, such as blind hole 29, through hole 28 and several threaded holes which can serve either as rod-support holes 27 or set-screw holes 23. It should be noted that the axes of these holes lie in one plane except that some are transverse to the others, e.g. holes 28 and 29.

As to K-wire holes it includes four vertical through and parallel holes 22 and two oblique holes 22a, one of which is shown in more detail in FIG. 5b. Such oblique K wire holes 22a can be included in any size block the angle of obliqueness may be selected for the particular application. The advantages realized with such holes is clearly appreciated by those familiar with the art. Briefly it enables a surgeon to support several K-wires which are not necessarily parallel to one another.

Figure 6:
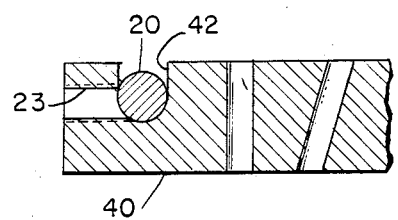
FIG. 6 is a cross-sectional view of a different type block.

In all of the foregoing described embodiments of blocks, the rod 20 extends in a hole is a block, be it a blind hole 29, a through hole 28 or a threaded hole 27. In some applications after the fixation system has been fixed to the hand it may be found advantageous to add one or more K wires between the distal and proximal blocks 12 and 13, respectively (see FIGS. 1 and 2) without disturbing the system. This may be achieved by adding a block to which rod 20 can be locked without disturbing the system. Such a block 40 is shown in FIG. 6 in cross-sectional view. This block instead of a rod supporting hole has an open cavity 42 into which a portion of the rod 20 between the distal and proximal blocks 12 and 13 ca be accommodated. A threaded hole 23 transverse to the cavity 42 is provided to enable a set screw 25 to lock the rod 20 to block 40 in cavity 42. Thus the block 40 can be attached between the distal and proximal blocks without disturbing the system. In FIG. 6 block 40 is shown with K-wire holes 22 and 22a, simply for explanatory purposes.

Figure 7:
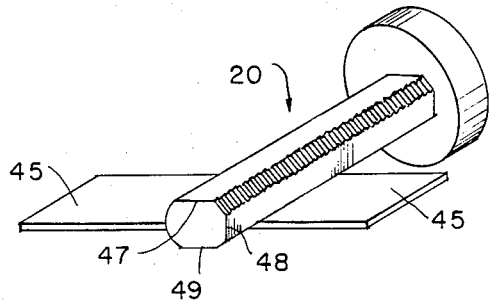
FIG. 7 is an isometric view of a rod 20 shown in FIGS. 1 and 2.

It should be appreciated that the rod 20 is capable of being locked to any block, with the block at any desired angular orientation with respect to an imaginary plane along which the rod extends. Assuming this plane to be one designated in FIGS. 7a by 45, any block can assume any angle up to 360°, with respect thereto. Thus the angle between blocks can be easily controlled to support K-wires secured in bones at different angular orientations. In order not to damage the threads on rod 20 by the pressing tips of set screws 25, if desired the rod may have several flat faces along its length, with the faces forming preselected angles therebetween. In FIG. 7 such faces are designated by 47–49, where flat face 47 is assumed to be in the plane 45 face 48 at 90° with respect thereto and face 49 at 180°. Clearly, faces at other angles may be formed.

Herebefore the invention has been described in the context in which a single straight rod, e.g. rod 20 with or without flat faces is used to support the spaced apart blocks. There are cases in treating hand injuries in which the bones adjacent the injury can form an angle between them or for therapeutic purposes such angles are formed in bending one part of finger with respect to another part. For example, in a troclear joint system the pivot point is eccentric. Thus, in such a system the distance between the pivot point on one bone with respect to a point on an adjacent bone is greater in flexion than when the adjacent bone is straight. To treat an injury at such a troclear joint system a rod arrangement other than a single straight rod 20 is required. Other requirements will become apparent from the following description.

Figure 8:
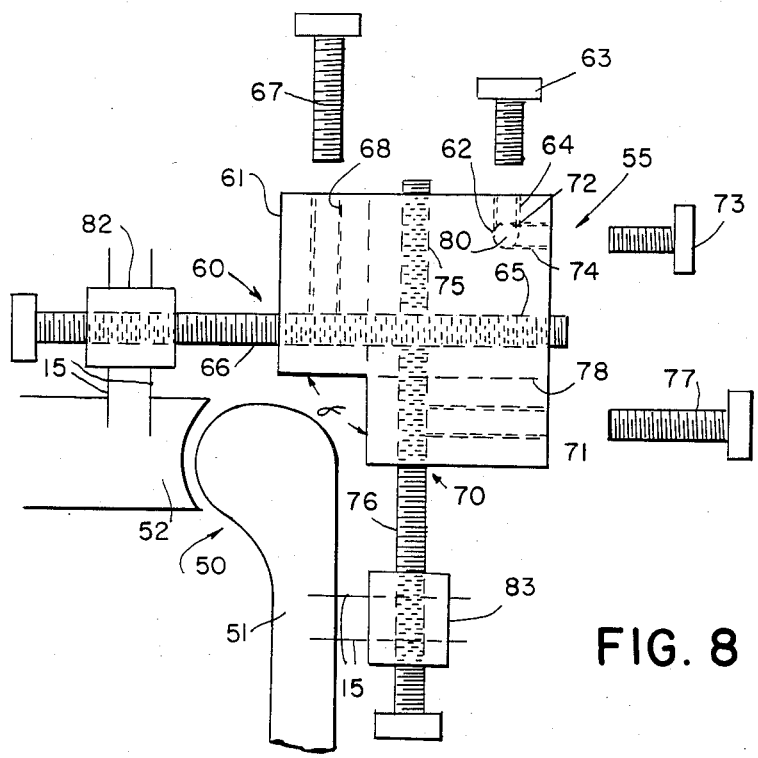
FIG. 8 is a diagram of yet another embodiment of the invention.

In FIG. 8 to which reference is now made a troclear eccentric joint 50 is shown in the bent state between bones 51 and 52. In order to treat an injury at such a joint to enable bending and straightening of bone 52 with respect to bone 51 a fixation system 55 made up of two similar subsystems which are pivotable so as to form a selected angle $\alpha$ therebetween is employed. The two subsystems are designated by numerals 60 and 70. Subsystems 60 and 70 include blocks 61 and 71 respectively which are releasably securable to a common pivot 80. The latter is in the shape of a short threaded bolt, preferably with a plurality of flat faces at selected angles and locations as will be explained hereafter. Each of blocks 61 and 71 which may be similar to block 12 with the four holes 22, or to block 35 (FIG. 5a) except that one of its holes parallel to holes 22 is larger and is threaded rather than a through hole. In FIG. 8 numeral 62 designates this hole of block 61 and is shown with joint bolt 80 threaded therethrough. Block 71 which is FIG. 8 is partially covered by upper block 61 has a similar hole 72 which is threaded and through which pivot bolt 80 extends. The two blocks can be adjusted to assume any desired angle $\alpha$ therebetween. Once the desired angle is assumed each block is lockable to the bolt 80. To this end set screws 63 and 73 are provided, which are threaded into threaded holes 64 and 74 in blocks 61 and 71, respectively. These latter mentioned holes and screws are similar to holes 23 and 24 except that instead of being used to lock a K-wire to a block, in this embodiment they are used to clamp the blocks 61 and 71 to the pivot bolt 80.

Blocks 61 and 71 also have through holes 65 and 75 through which individual block supporting rods 66 and 76 of the two subsystems extend. These rods are lockable to their respective rods by long set screws 67 and 77 which are threadable in threaded holes 68 and 78.

Any one of the previously described blocks is locked onto the proximal portion of each of rods 66 and 76 with K-wires which extend into the two bones 51 and 52 clamped thereto. In FIG. 8 these blocks are designated by numerals 82 and 83, and the K wires by numerals 15. In FIG. 8 two K wires are shown extending from each of blocks 82 and 83. Clearly, if desired one or more than two such wires can be employed. Also, one or more of the K wires may be obliquely positioned by using a block with an oblique hole 22a, as previously described.

From the foregoing it should thus be apparent that with the fixation system 55 the troclear joint can be easily secured for treatment. Most importantly the joint can be exercised with little adjustments. For example, if for therapeutic reasons it is desired to straighten bone 52 with respect to bone 51, all that is needed is to loosen screws 63 and 73 in blocks 61 and 62 and screws 67 and/or 77 in blocks 61 and 71. The loosening of screws 63 and 73 frees the angular orientation between blocks 61 and 71 which are used only to support rods 66 and 76, thus enabling the two blocks to extend in a plane parallel to the straightened joint 50. By loosening screws 67 and/or 77 the rods within the blocks are repositionable to insure that blocks 82 and 83 are properly spaced for the new straight alignment of the troclear joint. Once the proper position has been attained the four set screws are retightened.

Figure 9:
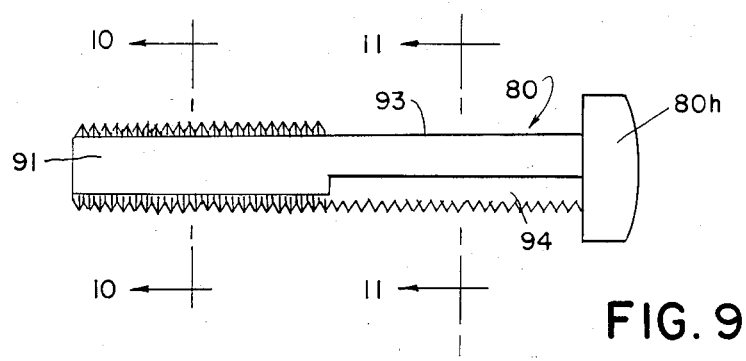
FIGS. 9–11 are diagrams useful in describing a novel pivot joint 80, shown in FIG. 8.
Figure 10:
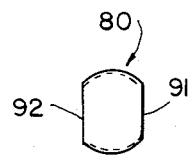
Figure 11:
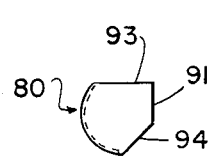

Typically, the number of values which the angle α has to assume for proper angular orientations between the two rods 66 and 76 is relatively small. Thus although one can use a bolt 80 with flat faces at particular angles, it is preferable to form a plurality of faces on the periphery of the bolt so that locking of either block 61 or 71 to the bolt 80 by set screw 63 or 73 is on a flat face of the bolt. One embodiment of such a bolt 80 is shown in FIG. 9 and in cross-sectional views along lines 10—10 and 11—11 in FIG. 9, in FIGS. 10 and 11, respectively.

Briefly, the bolt 80 has one flat face 91 extending along its entire length. In addition on its distal portion away from is head 80h it has an opposite flat face 92, which is parallel to face 91. As to its proximal portion, it has two additional faces 93 and 94. For example, face 93 is assumed to be at 90° with respect to face 91 while face 94 forms a 45° angle with face 91. With these flat faces the two blocks 61 and 71 can be oriented with respect to one another at any one of 45, 90 or 180 degrees.

Although particular embodiments of the invention have been described and illustrated herein, it is recognized that modifications and variations may readily occur to those skilled in the art and consequently, it is intended that the claims be interpreted to cover such modifications and equivalents.

I claim:

1. A versatile unilateral fixation system comprising:
   a rod element;
   first and second blocks, each block defining at least one aperture through which a wire is securable, the wire being adapted to have one end thereof secured within a hand bone, with the wires securable to the two blocks being secured in different hand organs;
   means for releasably attaching the two blocks to said rod so that the wires attached to the blocks are at a preselected orientation, with the distance between said blocks on said rod being controllable by rotating said rod;
   a first rod accommodating cavity located within the first block;
   wherein said rod defines a first end with means for facilitating said rod rotation with said first block proximal to said first end, and the second block defining a longitudinal blind ended cavity through which a distal end of said block extends, and said means for releasably attaching comprises means for fixedly attaching said block to said rod, for at least partially releasing said block so that said rod is free to rotate within said blind ended cavity without being removable therefrom.

2. A versatile unilateral fixation system as recited in claim 1 wherein said blind ended cavity only extends partially from one side of said second block toward a second opposite side and defines a bottom thereat, and said second block further defines a threaded opening extending transverse to said cavity for accommodating a set screw threadably extendable in said opening to press against the rod in said cavity and thereby effectively clamp said second block to said rod.

3. A versatile unilateral fixation system as recited in claim 2 wherein said rod is a threaded rod of a diameter definable as $D_R$, except for a portion near the distal end thereof whereat the rod is of a smaller diameter, said portion of reduced diameter being alignable with said opening when the rod's distal end abuts the cavity bottom.

4. A fixation system as recited in claim 1 wherein said first block proximal to the first end of said rod having a threaded rod accommodating cavity, with the rod being threaded whereby said rod is threadable in said cavity of said first block to control the position on said first block on said rod.

5. A fixation system as recited in claim 4 wherein said first block further defines a threaded opening transverse to said cavity and extending from the exterior of said block to the cavity to accommodate a threaded set screw therein to press the rod extending through the threaded cavity against said first block and thus secure the first block to the rod.

6. A fixation system as described in claim 1, wherein each aperture in a block for securing a wire thereto is a through aperture on the order of not more than several millimeters (mm), and the cavity in each block in which the rod is accommodatable being in a plane which is substantially transverse to the longitudinal axis of each of said aperture(s).

7. A fixation system as recited in claim 6 wherein each block further includes a threaded opening extending transversely to each aperture for facilitating a set screw to extend thereto to secure a wire extending through the aperture to the block.

8. A fixation system as recited in claim 7 wherein at least one of said blocks includes a second cavity for accommodating said rod therethrough the second cavity extending parallel to the rod accommodating cavity.

9. A fixation system as recited in claim 8 wherein the second cavity in a block extends transversely to the first cavity.

10. A fixation system as recited in claim 9 wherein the second cavity is a through hole of a diameter sufficient for the rod to freely extend therethrough.

11. A fixation system as recited in claim 9 wherein the second cavity is a threaded through hole and said rod is threaded to be threadable through said second cavity.

12. A fixation system as recited in claim 7 wherein at least one of said blocks includes a second cavity for accommodating said rod therethrough, the second cavity extending transverse to the rod accommodating cavity.

13. A fixation system as recited in claim 1 wherein at least one of said blocks includes a plurality of spaced apart apertures for securing wires thereto, each aperture being associated with a threaded opening extending thereto from the block exterior for enabling a set screw to be threaded therein and press against a wire extending through the aperture.

14. A fixation system as recited in claim 13 wherein each aperture is on the order of not more than several mm in diameter for accommodating a Kirschner type wire therein.

15. A fixation system as recited in claim 14 wherein all the apertures in a block are substantially parallel to one another.

16. A fixation system as recited in claim 14 wherein at least one of said apertures is slanted with respect to at least one other aperture.

17. A fixation system as recited in claim 1 further including a third block having at least one through aperture for accommodating a wire therein, and having an open cavity large enough to surround a portion of the rod therein, while said first and second blocks are secured to said rod.

* * * * *